(12) United States Patent
Aasmul

(10) Patent No.: US 7,869,042 B2
(45) Date of Patent: Jan. 11, 2011

(54) FLUOROMETERS

(75) Inventor: Søren Aasmul, Holte (DK)

(73) Assignee: PreciSense A/S, Horsholm (DK)

( * ) Notice: Subject to any disclaimer, the term of this patent is extended or adjusted under 35 U.S.C. 154(b) by 0 days.

(21) Appl. No.: 12/457,854

(22) Filed: Jun. 23, 2009

(65) Prior Publication Data

US 2010/0090126 A1 Apr. 15, 2010

Related U.S. Application Data

(63) Continuation of application No. 10/584,294, filed as application No. PCT/EP2004/014484 on Dec. 20, 2004, now Pat. No. 7,567,347.

(30) Foreign Application Priority Data

Dec. 23, 2003 (GB) ................... 0329849.4

(51) Int. Cl.
G01N 21/25 (2006.01)
(52) U.S. Cl. ..................................... 356/417
(58) Field of Classification Search .............. 356/417; 250/458.1
See application file for complete search history.

(56) References Cited

U.S. PATENT DOCUMENTS

| | | |
|---|---|---|
| 4,679,562 A | 7/1987 | Luksha |
| 5,194,393 A | 3/1993 | Hugl et al. |
| 5,277,872 A | 1/1994 | Bankert et al. |
| 5,342,789 A | 8/1994 | Chick et al. |
| 5,476,776 A | 12/1995 | Wilkins |
| 5,757,014 A | 5/1998 | Bruno et al. |
| 5,801,828 A | 9/1998 | Collins |
| 6,002,954 A | 12/1999 | Van Antwerp et al. |
| 6,018,387 A | 1/2000 | Eppler et al. |
| 6,256,522 B1 | 7/2001 | Schultz |
| 6,355,934 B1 | 3/2002 | Oosgood et al. |
| 6,809,859 B2 * | 10/2004 | Erdogan et al. ............. 359/359 |
| 6,927,246 B2 | 8/2005 | Noronha et al. |
| 7,045,361 B2 | 5/2006 | Heiss et al. |
| 7,297,548 B2 | 11/2007 | Kawanishi et al. |
| 7,567,347 B2 | 7/2009 | Aasmul |

(Continued)

FOREIGN PATENT DOCUMENTS

JP 07-243970 9/1995

(Continued)

OTHER PUBLICATIONS

Japanese Office Action and English Translation for corresponding Japanese Application No. 2006-546024, mailed May 25, 2010, 5 pages.

Primary Examiner—Tarifur Chowdhury
Assistant Examiner—Abdullahi Nur
(74) Attorney, Agent, or Firm—Nixon & Vanderhye P.C.

(57) ABSTRACT

In apparatus for the production and detection of fluorescence at a sample surface, the height of the apparatus above the sample surface is reduced, and loss of the emitted fluorescence due to reflection loss and light scattering is minimized. The apparatus comprises a three-dimensionally curved light reflecting surface (40) that directs light from a light source (32) transversely to its original path and focuses the light on to an illumination zone (30) at or below the sample surface. The reflecting surface (40) also collects, directs and at least partially collimates emitted fluorescence transversely to its original path and towards a detector (46).

14 Claims, 10 Drawing Sheets

U.S. PATENT DOCUMENTS

2001/0033381 A1  10/2001  Stumbo et al.
2002/0060791 A1* 5/2002  Stumbo et al. .............. 356/317

FOREIGN PATENT DOCUMENTS

| JP | 2000-235147 | 8/2000 |
| JP | 2001-074656 | 3/2001 |
| WO | WO 00/02048 | 1/2000 |
| WO | WO 02/30275 A1 | 4/2002 |
| WO | WO 03/002973 A2 | 1/2003 |

* cited by examiner

FLUOROMETERS

CROSS REFERENCE TO PRIORITY APPLICATIONS

This application is a continuation of U.S. application Ser. No. 10/584,294, filed Dec. 14, 2006, now U.S. Pat. No. 7,567,347, which application is the U.S. national phase of international application PCT/EP2004/014484 filed Dec. 20, 2004 which designated the U.S. and claims benefit of GB 0329849.4 filed Dec. 23, 2003, each incorporated by reference in its entirety.

The present invention relates to fluorometers, being apparatus for producing and measuring fluorescence, whether using intensity or time resolved measurements.

Epifluorescence microscopes conventionally have a linear optical arrangement in which a sample location, beam splitter and detector are arranged spaced, for instance vertically, along a common axis in a first direction, with an excitation light source off to one side. This arrangement dictates a minimum height constraint so as to provide room for fluorescence light emitted from a sample location to be collimated by a lens system, passed through the beam splitter, filtered to remove wavelengths other than that of the fluorescence and finally to be focussed onto the detector. Such a conventional arrangement is illustrated in FIG. 1 as discussed in greater detail below. In fluorescence applications the intensity of the emitted fluorescence is usually weak. Furthermore, the fluorescence is emitted isotropically or according to a Lambertian radiation pattern if the fluorophore is situated in a light scattering medium such as skin. In both cases the detected fluorescence increases with the numerical aperture of the optical system. In the common epifluorescence set-up a large numerical aperture is normally obtained by the use of a number of lenses, which introduces reflection loss and light scattering even for coated lenses.

It would be desirable to develop an alternative general optical arrangement with reduced complexity that can be used to reduce the necessary height of the apparatus measured from a sample location.

Accordingly, the present invention now provides in a first aspect apparatus for the production and detection of fluorescence at or below a surface, said apparatus comprising:
- a light source for directing fluorescence excitation light along a light path extending over a said surface;
- a reflector having a three dimensionally curved, shell-like light reflecting interface positioned to receive light from the light source passing over said surface along a portion of said light path and to reflect said light transversely with respect to said portion of the light path so as to focus said light on an illumination zone at or below said surface for stimulation of fluorescence at said zone, and to collect fluorescence light emitted at said zone and to reflect and at least partially collimate said light to pass back along said portion of the light path; and
- a detector for receiving said light emitted as fluorescence after reflection at said interface.

The 'surface' referred to above may be a physical surface defined by an interface between two different materials or may be a virtual surface definable with respect to the apparatus.

The apparatus may further comprise a beam splitter reflecting light emitted by said light source to pass to said reflector and receiving fluorescence light from said reflector and passing said fluorescence light to said detector.

Said reflector, light source and detector are preferably arranged in a generally coplanar manner and said beam splitter preferably has a planar reflective interface that lies in a plane orthogonal to the co-planarity of the reflector, light source and detector.

The apparatus may further comprise an excitation filter selecting an excitation wavelength from the light emitted by the light source to pass to said reflector.

The apparatus may further comprise an emission filter selecting an emitted fluorescence wavelength to pass to said detector.

The apparatus may comprise a lens focussing fluorescence light on said detector. Alternatively, a further focussing reflective interface may be used.

The or each said reflector interface may substantially have the form of a partial paraboloid, aspheric, toroidal, or biconic surface. Such a reflector interface may be paraboloid, aspheric, toroidal, or biconic surface. Spheric surfaces and aspheric surfaces such as hyperbolas, parabolas, ellipsoids and oblate ellipsoid reflector interfaces may be defined by an equation $$Z = \frac{cr^2}{1 + \sqrt{1 - (1+k)c^2r^2}}$$

wherein:

c is from 0.07 to 0.5 and k is from −1.5 to −0.7, where z is the "sag" of z-coordinate along the rotational axis, c is the curvature (the reciprocal of the radius R), k is the conical constant and r is the radial coordinate. Other surfaces may be described by similar equations involving an added Taylor expansion. Similarly, equations are available for toroids, e.g. faceted toroids, or piecewise linear toroids and for biconic surfaces.

The reflector interface of the reflector directing light to the illumination zone may include that part of a paraboloid, aspheric, toroidal, or biconic surface that is generated by the cutting of a paraboloid, aspheric, toroidal, or biconic surface by a right circular cylinder erected centred on the illumination zone.

Said reflector interface may preferably substantially have the form of a part of a half paraboloid.

The apparatus may further include a housing containing the light source, reflector and detector and having a base surface containing a window for passing excitation light out of the housing and receiving fluorescence light into the housing and being for engagement in use against the said surface at or below which said fluorescence occurs.

Preferably, said light path makes an angle of no more than 10 degrees with a plane defined by said base surface.

The invention will be further described and illustrated with reference to the accompanying drawings in which.

Figure 1:
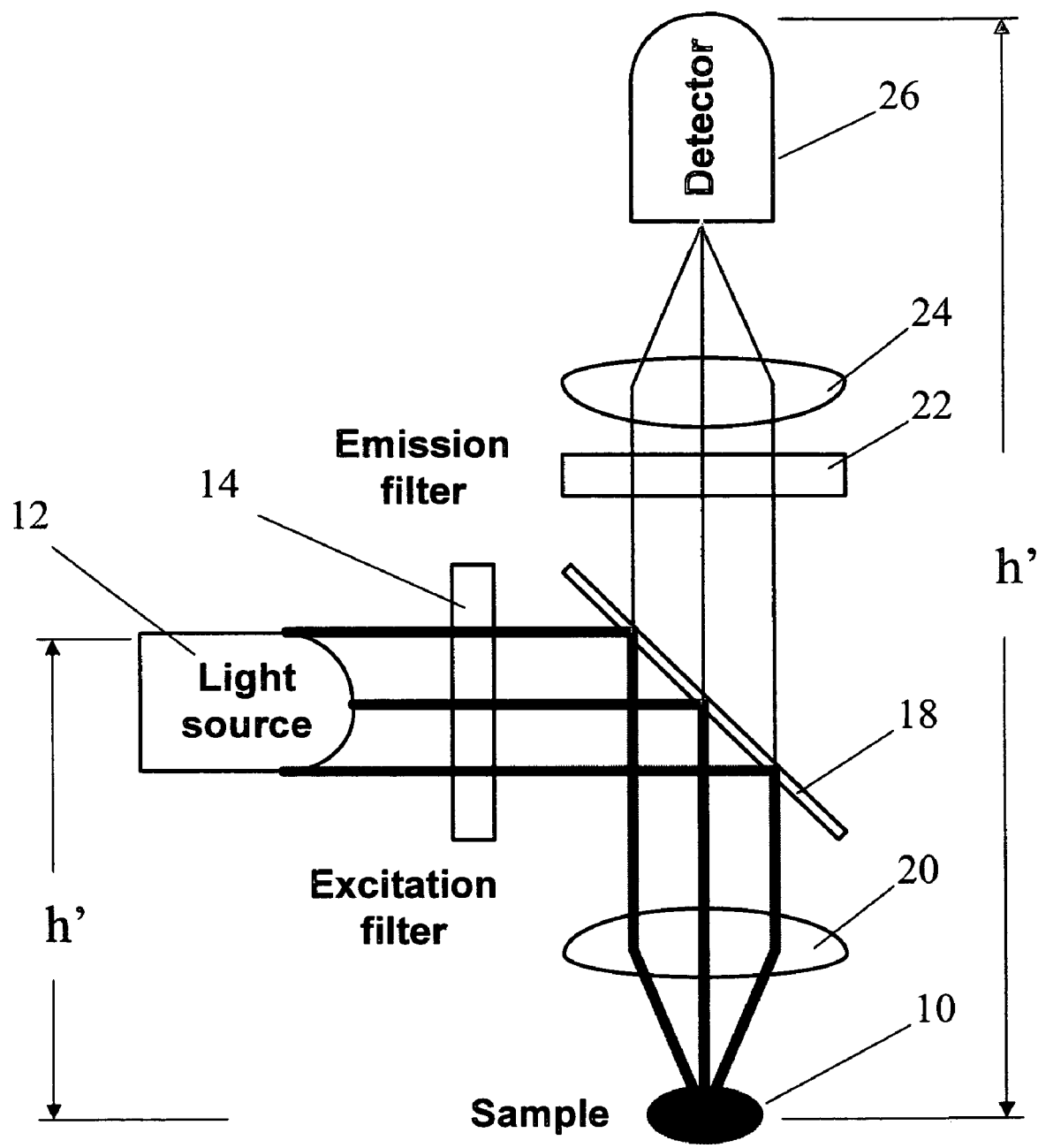
FIG. 1 is a schematic side elevation view of a conventional epifluorescence measuring apparatus.

A common set up for epifluorescence measurement is shown in FIG. 1. It is designed for producing and detecting fluorescence at a sample location 10, which might be for instance at or below the surface of a body or article, e.g. on a microscope slide. Typically such a surface will be horizontal and for convenience, this is assumed in the following description of the apparatus. An excitation light source 12, such as an LED, is positioned off to one side of the sample location 10 and at a height h above the sample location. The LED emits excitation light 16 which is passed through an excitation filter 14 to select a desired excitation wavelength. The excitation light falls on an angled beam splitter 18 such as a parallel sided dichroic beam splitter 18. A portion of the excitation light is reflected down at right angles towards the sample location and passes through a focussing lens system 20 comprising one or more simple or compound lenses.

Fluorescence and reflected excitation light emanating from the sample location are captured by the lens system 20 and collimated into a parallel beam which passes through the beam splitter 18 to an emission filter 22, which ideally removes all but the fluorescence wavelength, and from there to a second lens system 24 that focuses the fluorescence onto a detector 26. Like the lens system 20, the lens system 24 may comprise one or more simple or compound lenses.

The whole device has a total height above the sample of h', which is around 3×h.

It has been proposed to monitor concentrations of chemical species in the human or animal body by fluorescence based techniques. These would involve directing the excitation light onto the skin and detecting fluorescence emission from the skin. Relevant teachings include WO00/02048 and WO02/30275.

We have noted that it would be desirable in such circumstances and others to reduce the dimension h' of the fluorescence detection apparatus used.

Figure 2:
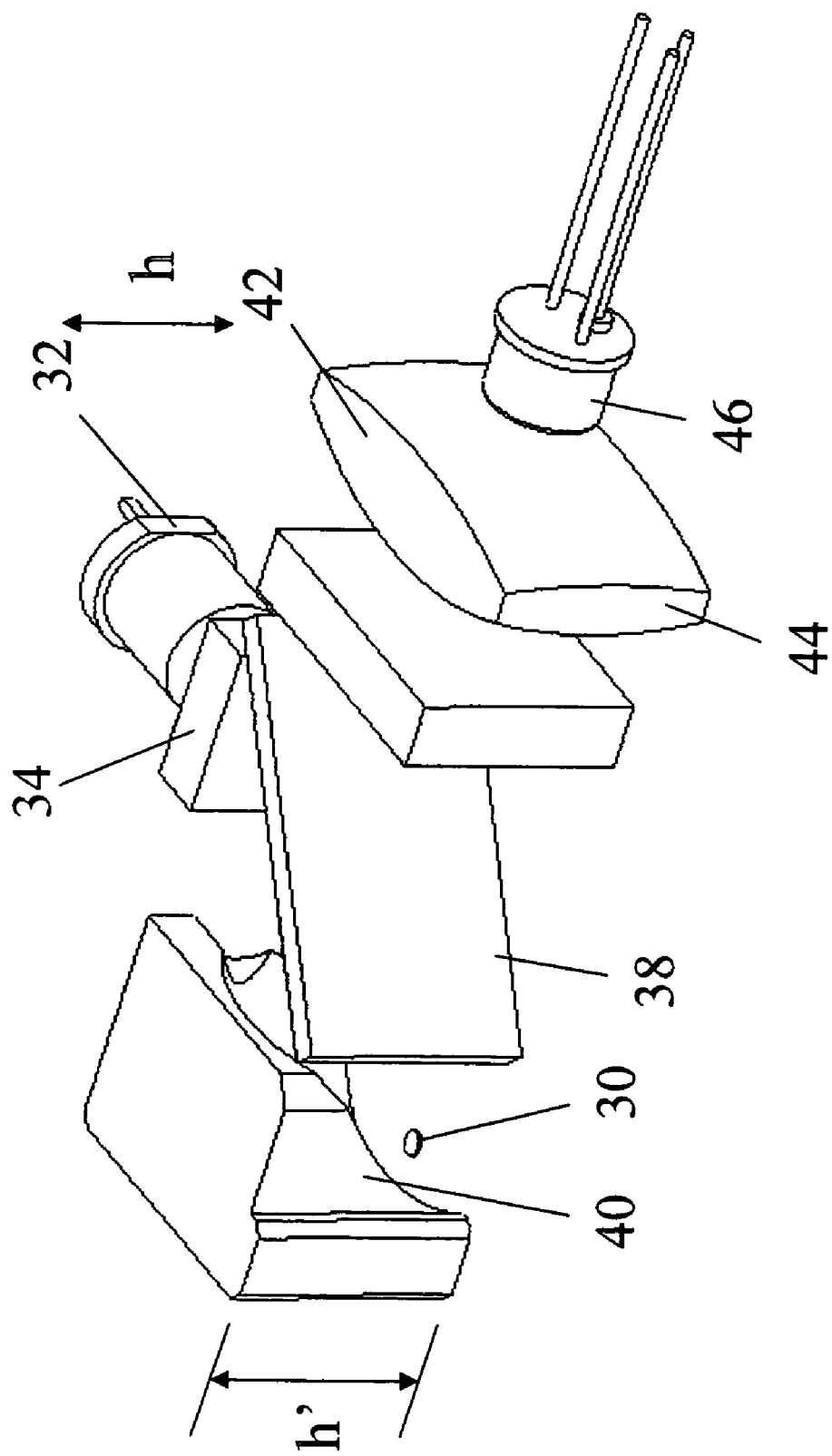
FIG. 2 is a perspective view of a first embodiment of apparatus according to the present invention.

FIG. 2 shows an embodiment of apparatus according to the invention. Here, the apparatus is depicted placed on the surface of the skin or a similar surface on which fluorescence is to be detected. For convenience in the following description, the plane of the skin will be treated as being horizontal. A light source 32 emits light along a path parallel to the skin surface, and determines a height h for the apparatus which approximately equals to the total height h' of the device.

The light passes through an excitation filter 34 to a dichroic beam splitter 38 disposed in a vertical plane and is diverted towards a half paraboloid shaped mirror reflector 40 which replaces the lens system 20 of the conventional apparatus. The reflector focuses the light down onto an illumination zone 30 on the skin surface or towards an illumination zone just below the skin surface. The reflector collects and collimates fluorescence emissions from the illumination zone and directs the emitted light back to the beam splitter, which it passes through to reach an emission filter 42. From there, the light is focused by a lens system 44 of the same type as lens system 24 and is detected at a detector 46.

It can be seen that the vertical height of the apparatus has been reduced from approximately 3×h in FIG. 1 to just h in FIG. 2.

Generally, interference filters are used in fluorometers as the excitation and emission filters. These require that the incident light be orthogonal to the plane of the filter if the expected wavelength passing properties are to be obtained, because with obliquely incident light, the filter pass band will be shifted towards shorter wavelengths. Collimation of the light beams incident on these filters is therefore required.

The paraboloid reflector 40 may be constructed in a number of ways to produce a reflecting interface of the desired shape. For instance, the interface may be between air inside the paraboloid and a reflective concave interior surface of a body. Alternatively, the interface may be formed at the convex exterior surface of a solid hemi-paraboloid member, for instance a silvered exterior of a glass or plastics hemi-paraboloid block.

Figure 6:
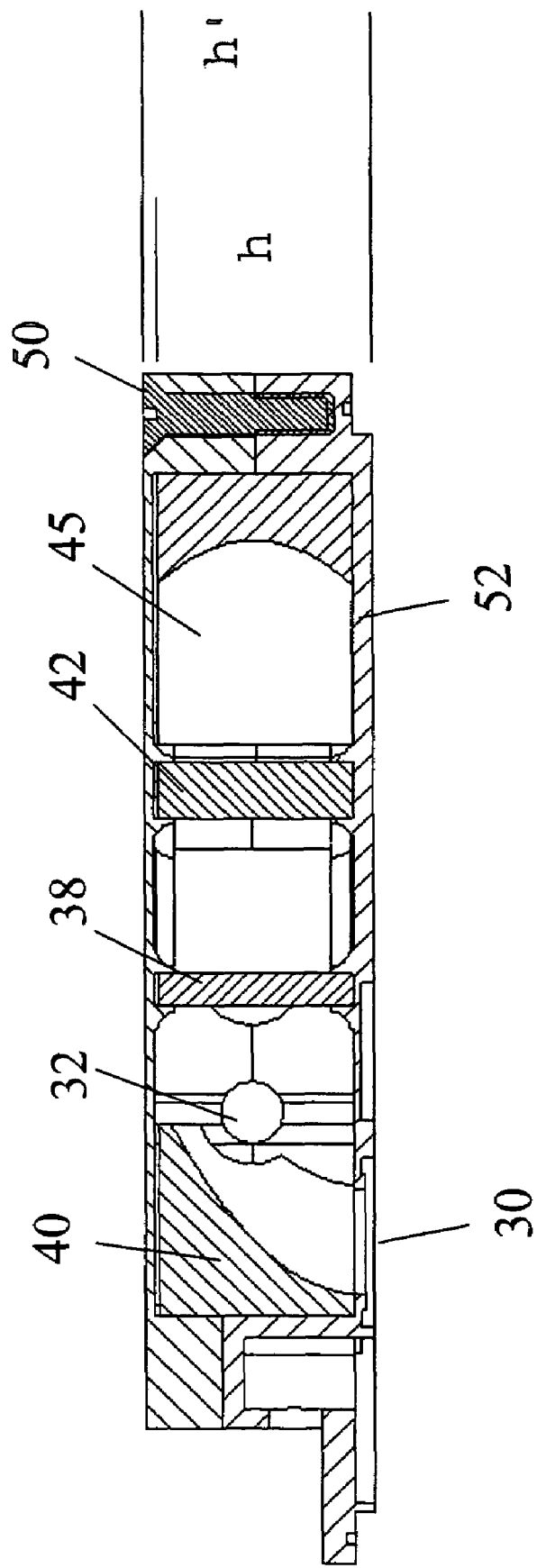
FIG. 6 is a cross section on the line VI-VI' marked in FIG. 4.

The whole of the illustrated apparatus will be bounded by a housing or casing (as seen in FIG. 6) having a bottom face containing an aperture which may be filled with a transparent window (suitably of glass, silica or in some applications plastics) for protecting the optics against dust and humidity and for allowing the passage of excitation and fluorescence light to and from a sample in the illumination zone. Said apparatus may thus be a simple opening in the casing or an optical window.

Signals from the detector may be fed to suitable electronic circuitry for analysis in a known manner. The LED may be powered by suitable electronic circuitry as known and the LED supply circuitry and the detected signal processing circuitry will generally form part of an integral circuitry for producing intensity based or time resolved (frequency domain) measurements of the fluorescence, e.g. in a FRET (fluorescence resonance energy transfer) based assay.

The illustrated apparatus provides a high numerical aperture for the capture of fluorescence from the illumination zone whilst enabling a compact optical geometry suited for use where space is at a premium, e.g. in a device to be worn on the body.

Not all of the illustrated paraboloid surface is needed in order to obtain good results. The paraboloid need not, as shown, be arranged with its axis coincident with the surface on which the device is to be used but may be angled up to gain some additional height above the surface for the detector optics. The beam of fluorescent light may not be collimated entirely by the reflector but may in part be collimated by an auxiliary lens system. The physical illumination zone of the apparatus need not lie at the focus of the reflector. The reflector interface need not be in the form of a true paraboloid. These concepts are further illustrated in subsequent Figures.

Figure 3:
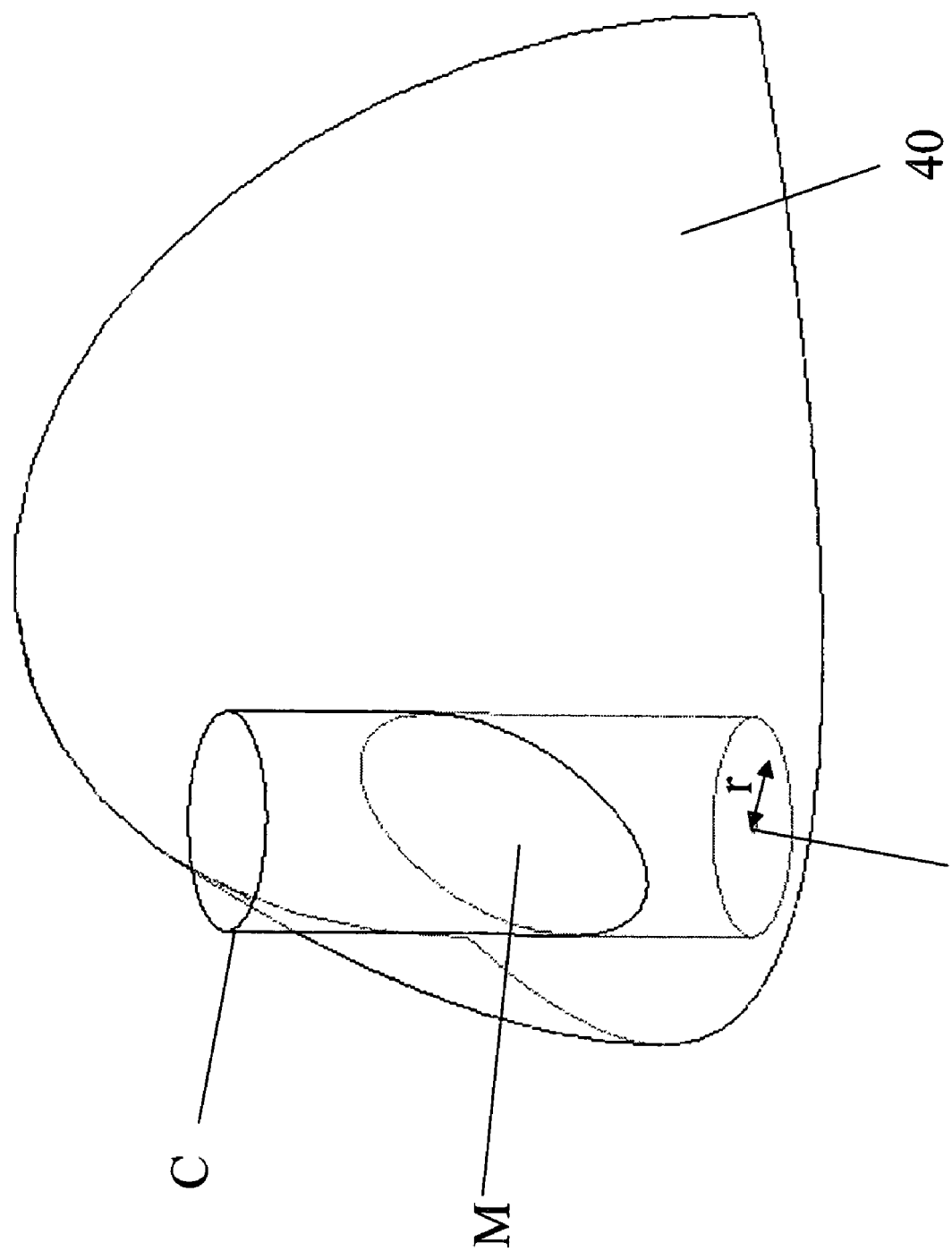
FIG. 3 is an illustration showing the zone of a parabolic mirror in which most energy is collected when light is emitted from a surface over which the mirror lies.

As shown in FIG. 3, the area of the paraboloid surface M that will receive and collimate out to the detector most of the fluorescence emitted from the illumination zone will be that defined by the intersection of a right circular cylinder C centred on the illumination zone with the paraboloid surface itself. The remainder of the paraboloid surface need not therefore be present. Clearly, the smaller the cylinder, the less light will be captured, so preferably at least as much of the paraboloid is present as is defined by the intersection with a cylinder of a radius r not less than 50%, preferably not less than 75%, more preferably not less than 90% of the distance marked f from the origin to the focal point of the paraboloid. The radius r of the cylinder need not be smaller than the focal length of the parabolic mirror, as in the case shown in FIG. 3, but can be larger.

Figure 4:
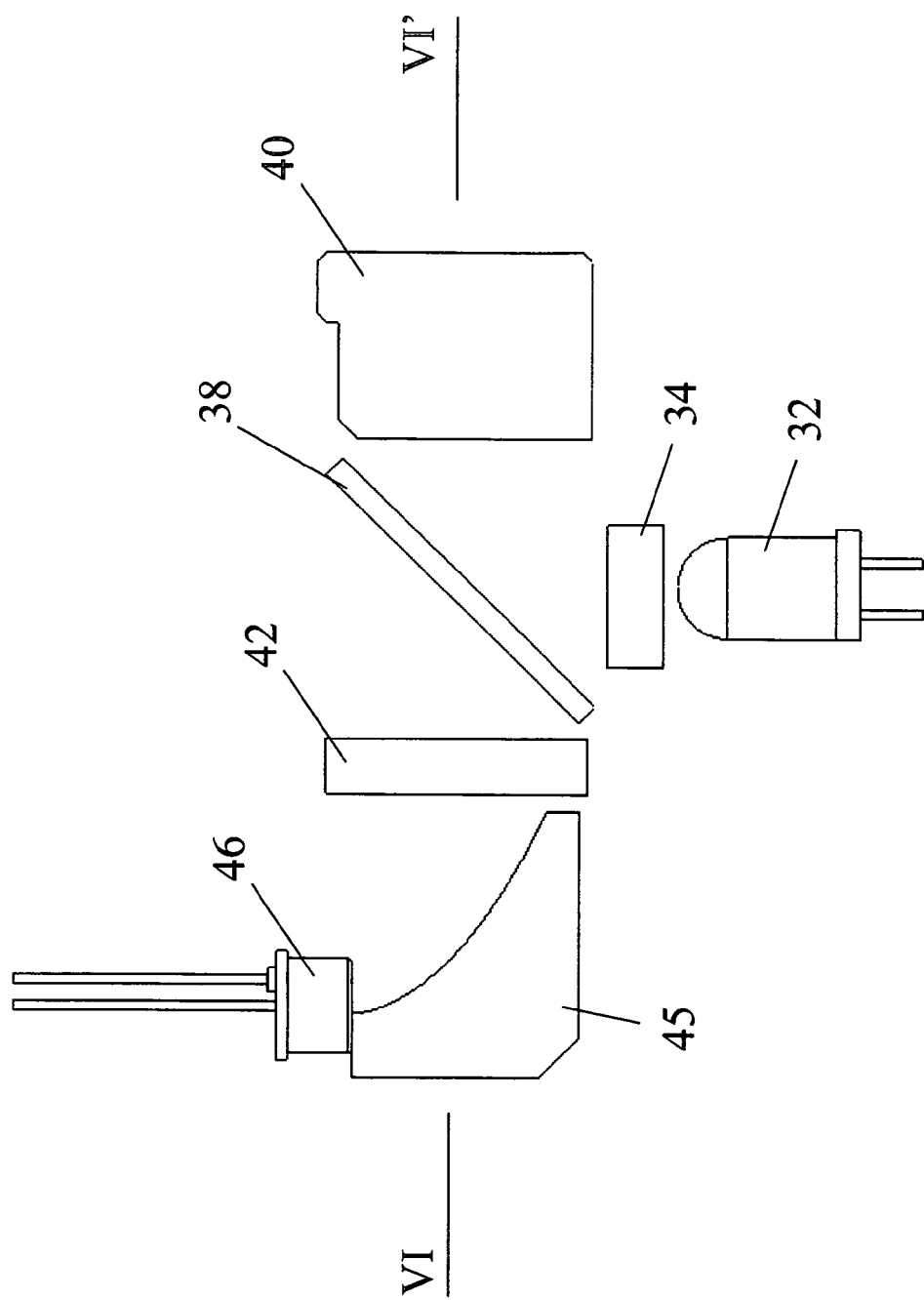
FIG. 4 is a plan view from above of a second embodiment according to the invention.
Figure 5:
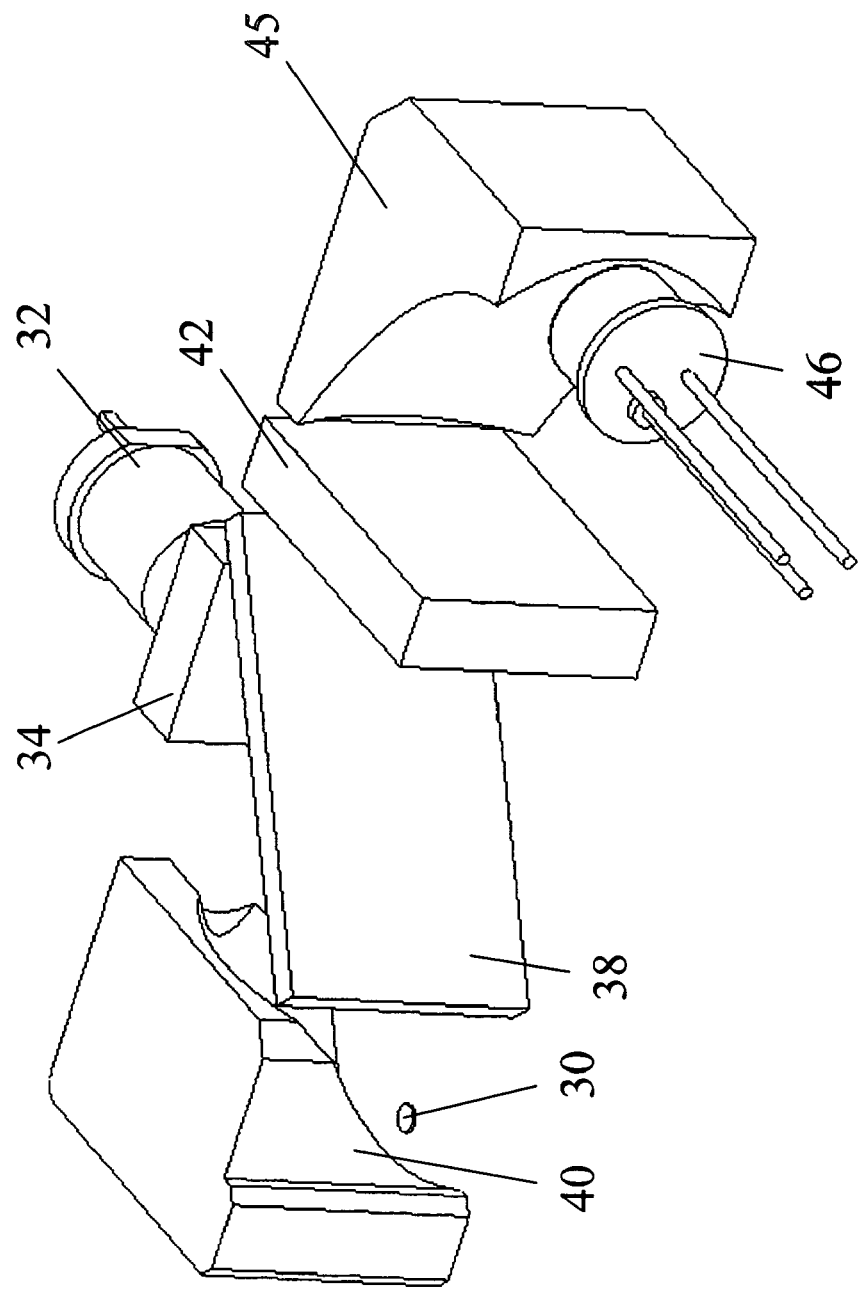
FIG. 5 is a perspective view of the apparatus of FIG. 4.

Whilst in FIG. 2 a lens system is shown focusing the light onto the detector, it will be appreciated that this could also be a reflector system instead, which might suitably resemble that used to focus the excitation light on the illumination zone. Such a system is shown in FIGS. 4 to 6.

In the illustrated apparatus, the illustrated components are as in FIG. 2 except that the lens system 44 is replaced by a part parabolic mirror 45 which resembles mirror 40 but is arranged to focus the fluorescence light to the side where the detector 46 is now positioned. As seen in FIG. 6, the apparatus comprises a housing 50 having a base plate 52 lying on the skin and containing a window 54 as previously described which defines the illumination zone 30. The housing comprises upper and lower half shells having internal formations to cradle and support the optical components, the shells being secured together by screws as shown.

Figure 7:
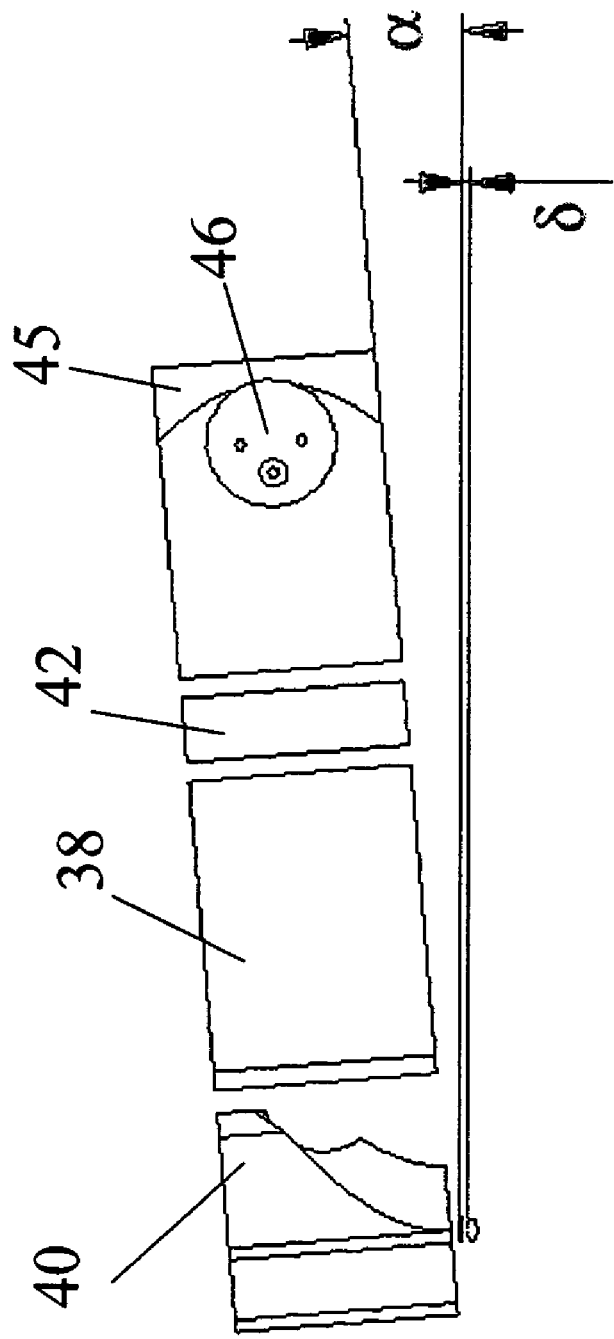
FIG. 7 shows a modification of the apparatus of FIG. 4.

As shown in FIG. 7, the base surface of the housing may lie at an angle α, preferably not exceeding 10°, more preferably not exceeding 5°, to the axis of the paraboloid surface. This will give some additional space for the optical and electronic components but will also result in some additional height at the detector end of the apparatus. This modification may be employed both in relation to the embodiment using mirrors at each end as shown and in relation to the embodiment of FIG. 2. Furthermore, the focal point of the mirror 40 may differ from the location of the sample, as shown on FIG. 7 by the distance δ, in order to compensate for the radiation pattern and scattering properties of the sample or surrounding media as in the case of detecting fluorescence under the skin.

Figure 8:
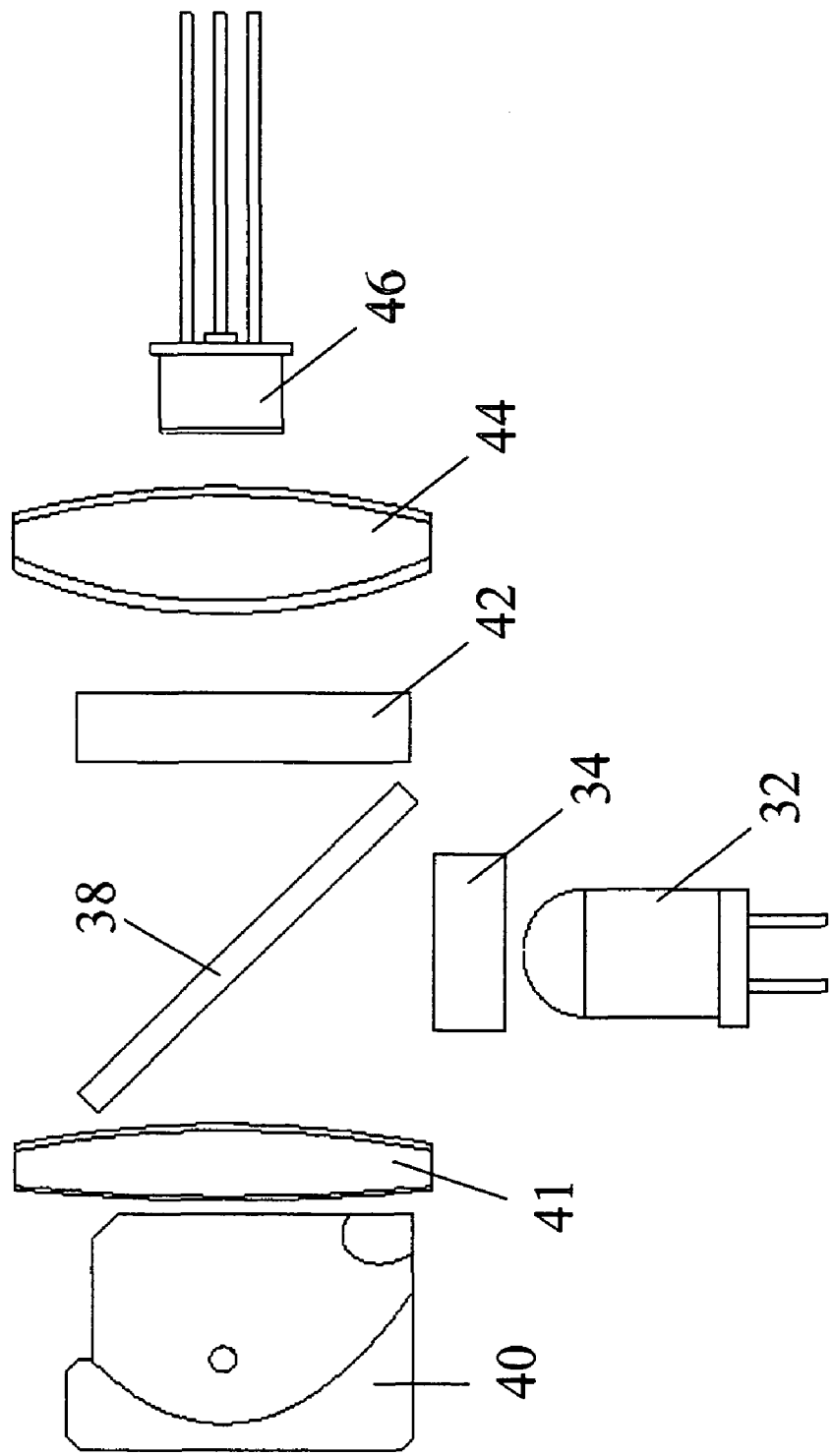
FIG. 8 shows a third embodiment according to the invention in plan from above.

As shown on FIG. 8, an auxiliary lens system comprising one or more simple or compound lenses 41 positioned in front of mirror 40 may be used to produce further collimation.

Similarly, the shape of the reflector may deviate from that of a paraboloid in order to accommodate to the radiation pattern and scattering properties of the sample or surrounding media as in the case of detecting fluorescence under the skin. If this leads to an incomplete collimation of the fluorescence emissions, further collimation may be carried out using an auxiliary lens system 41 as illustrated.

Alternative curved surfaces that may be used include toroidal, aspheric and biconic surfaces.

Figure 9:
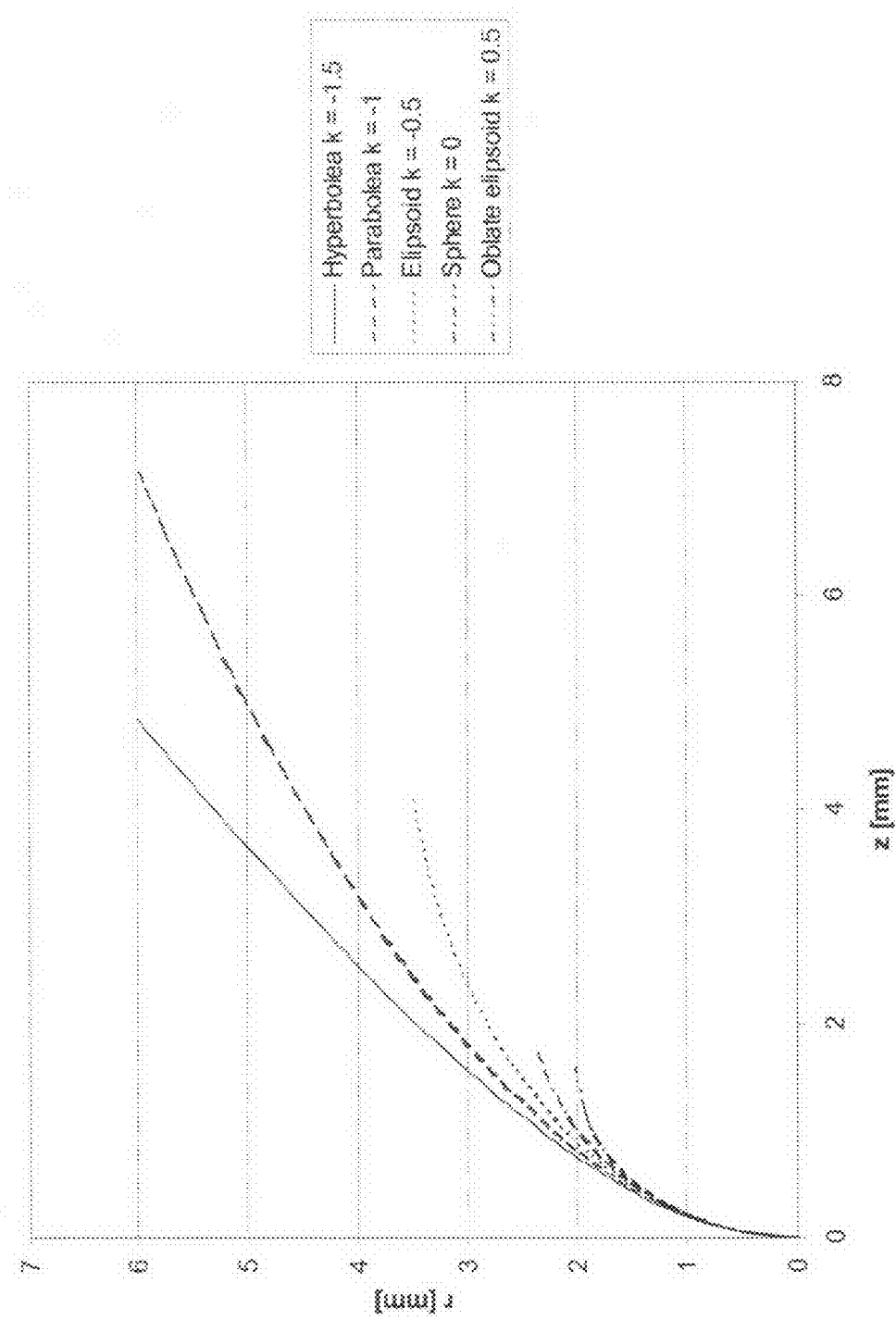
FIG. 9 is a graph of the variation in shape of a parabolic mirror with the conical constant.

For an aspheric surface defined by $$Z = \frac{cr^2}{1 + \sqrt{1 - (1+k)c^2 r^2}}$$

c is preferably within the range of 0.07 to 0.5 and k is preferably within the range of −1.5 to −0.7, where z is the "sag" of z-coordinate along the rotational axis, c is the curvature (the reciprocal of the radius R) and k is the conical constant and r is the radial coordinate. The shape of the mirror is shown in FIG. 9 for various values of the conical constant.

Figure 10:
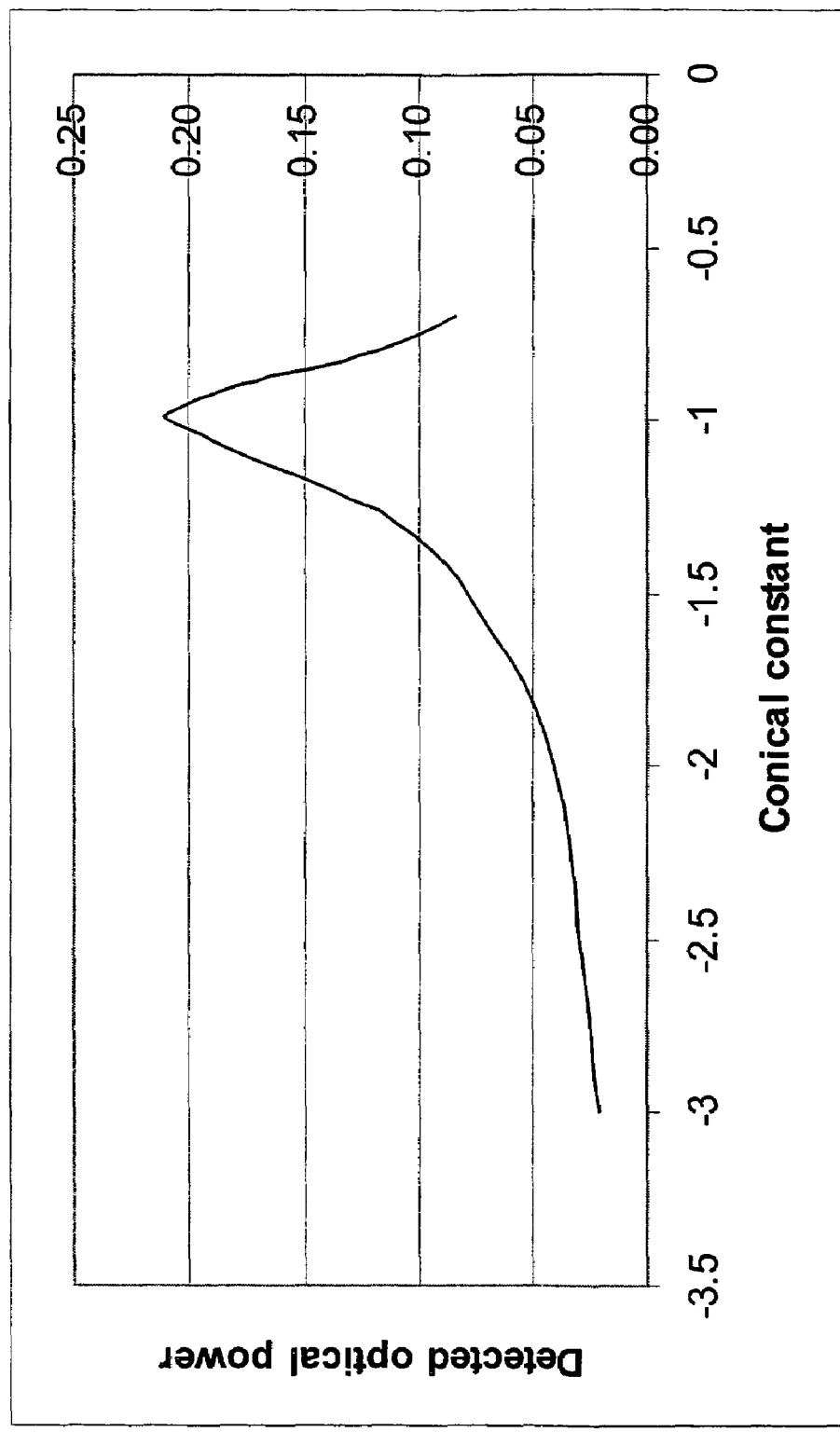
FIG. 10 is a graph showing the variation in the ratio of detected optical power and illumination power with changing conical constant.

In FIG. 10 the influence of the conical constant on the detected optical power is shown.

The illumination zone need not be a point or a circular area but by the effect of the use of non-paraboloid reflector shapes may be elongated either transversely or longitudinally of the axis of the reflector.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'.

The invention claimed is:

1. Apparatus to be worn on the body for the production and detection of fluorescence at or below a surface, said apparatus comprising:

a light source for directing fluorescence excitation light along a light path extending over said surface;

a reflector having a three dimensionally curved, shell-like light reflecting interface positioned to receive light from the light source passing over said surface along a portion of said light path and to reflect said light transversely with respect to said portion of the light path so as to focus said light on an illumination zone at or below said surface for stimulation of fluorescence at said zone, and to collect fluorescence light emitted at said zone and to reflect and at least partially collimate said light to pass back along said portion of the light path;

a detector for receiving said light emitted as fluorescence after reflection at said interface; and a housing containing the light source, detector and reflector, which housing is configured to be worn on the body, wherein the whole of the light paths from the light source to the reflective interface and from the reflective interface to the detector extend over the said surface.

2. Apparatus as claimed in claim 1, further comprising a beam splitter reflecting light emitted by said light source to pass to said reflector and receiving fluorescence light from said reflector and passing said fluorescence light to said detector.

3. Apparatus as claimed in claim 2, wherein said reflector, light source and detector are arranged in a generally coplanar manner and said beam splitter has a planar reflective interface that lies in a plane orthogonal to the co-planarity of the reflector, light source and detector.

4. Apparatus as claimed in claim 1, further comprising an excitation filter selecting an excitation wavelength from the light emitted by the light source to pass to said reflector.

5. Apparatus as claimed in claim 1, further comprising an emission filter selecting an emitted fluorescence wavelength to pass to said detector.

6. Apparatus as claimed in claim 1, comprising a lens or a second reflector focussing fluorescence light on said detector.

7. Apparatus as claimed in claim 1, wherein said reflector interface substantially has the form of a partial paraboloid, aspheric, toroidal, or biconic surface.

8. Apparatus as claimed in claim 7, wherein said reflector interface is defined by an equation $$Z = \frac{cr^2}{1 + \sqrt{1 - (1+k)c^2 r^2}}$$

wherein:

c is from 0.07 to 0.5 and k is from −1.5 to −0.7, where z is the "sag" of z-coordinate along the rotational axis, c is the curvature (the reciprocal of the radius R), k is the conical constant and r is the radial coordinate.

9. Apparatus as claimed in claim 7, wherein said reflector interface includes that part of a paraboloid, aspheric, toroidal, or biconic surface that is generated by the cutting of a paraboloid, aspheric, toroidal, or biconic surface by a right circular cylinder erected centred on the illumination zone.

10. Apparatus as claimed in claim 7, wherein said reflector interface substantially has the form of a part of a half paraboloid.

11. Apparatus as claimed in claim 1, wherein the housing containing the light source, reflector and detector has a base surface containing a window for passing excitation light out of the housing and receiving fluorescence light into the housing and being for engagement in use against the said surface at or below which said fluorescence occurs.

12. Apparatus as claimed in claim 1, wherein said light path makes an angle of no more than 10 degrees with a plane defined by said base surface.

13. Apparatus as claimed in claim 1, wherein the relative positions of the light source, detector and reflector are fixed in use.

14. Apparatus for the production and detection of fluorescence at or below a surface, said apparatus comprising:
- a light source for directing fluorescence excitation light along a light path extending over a said surface;
- a reflector having a three dimensionally curved, shell-like light reflecting interface positioned to receive light from the light source passing over said surface along a portion of said light path and to reflect said light transversely with respect to said portion of the light path so as to focus said light on an illumination zone at or below said surface for stimulation of fluorescence at said zone, and to collect fluorescence light emitted at said zone and to reflect and at least partially collimate said light to pass back along said portion of the light path; and
- a detector for receiving said light emitted as fluorescence after reflection at said interface;

wherein said reflector interface substantially has the form of a partial paraboloid, aspheric, toroidal, or biconic surface, and wherein said reflector interface is defined by an equation $$Z = \frac{cr^2}{1 + \sqrt{1 - (1+k)c^2 r^2}}$$ wherein:

c is from 0.07 to 0.5 and k is from −1.5 to −0.7, where z is the "sag" of z-coordinate along the rotational axis, c is the curvature (the reciprocal of the radius R), k is the conical constant and r is the radial coordinate.

* * * * *